United States Patent [19]

Kessidis

[11] Patent Number: 4,473,670

[45] Date of Patent: Sep. 25, 1984

[54] SALT-FILLED ABSORBABLE POLYMERS

[75] Inventor: George N. Kessidis, Princeton, N.J.

[73] Assignee: Ethicon, Inc., Somerville, N.J.

[21] Appl. No.: 497,946

[22] Filed: May 25, 1983

[51] Int. Cl.³ .............................................. C08K 3/10
[52] U.S. Cl. ................................... 523/105; 523/113; 524/401
[58] Field of Search .................... 524/401; 128/335.5, 128/334 R, 337; 523/105, 113

[56] References Cited

U.S. PATENT DOCUMENTS

| | | | |
|---|---|---|---|
| 3,225,766 | 12/1965 | Baptist et al. | 128/335.5 |
| 3,297,033 | 1/1967 | Schmitt et al. | 128/335.5 |
| 4,084,034 | 4/1978 | Jansma et al. | 524/401 |
| 4,410,599 | 10/1983 | Roe et al. | 524/401 |

Primary Examiner—Lewis T. Jacobs
Attorney, Agent, or Firm—Charles J. Metz

[57] ABSTRACT

Synthetic absorbable polymers contain finely divided sodium chloride or potassium chloride as a filler.

6 Claims, No Drawings

SALT-FILLED ABSORBABLE POLYMERS

The invention relates to the use of sodium chloride or potassium chloride as a filler for absorbable polymers.

BACKGROUND OF THE INVENTION

In many polymer applications, the polymers are not used in the pure state; rather, they are compounded with various additives to modify certain properties. For instance, it is well known to add fiberglass reinforcements to polymers to improve their mechanical properties.

Absorbable polymeric materials have been used in surgical applications for many years. For instance, gut sutures have been used since the nineteenth century. More recently, synthetic absorbable polymers have been used in surgical applications; first as sutures, and then as other implantable devices such as prostheses, supports, anastomotic devices, staples, and the like.

For many proposed surgical applications, it would be desirable to enhance certain of the strength properties of synthetic absorbable polymers. Obviously, however, the conventional reinforcing materials such as fiberglass cannot be used to reinforce articles that are to be left in the body to be absorbed. In order to qualify for use as a reinforcing agent in an absorbable article, the reinforcing agent must itself be absorbable and must exhibit no adverse reaction with body tissues.

This invention provides absorbable polymers containing a filler that meets the above criteria. Not only does the filler used in this invention enhance certain mechanical properties, such as stiffness, but it can also enhance the absorption rate of the polymer (by accelerating the absorption rate and/or making it more predictable), and can enhance the processing characteristics of the polymer.

SUMMARY OF THE INVENTION

The invention provides synthetic absorbable polymers which contain finely divided sodium chloride or potassium chloride as a filler to enhance certain properties, such as stiffness, absorption rate, processing characteristics, or the like, of the polymer.

THE PRIOR ART

It is known to add sodium chloride to a polymeric article while the article is being fabricated, for the purpose of incorporating in the article a substance that can be leached with a solvent to form porosity in that article.

It is known to add absorbable fillers to a synthetic absorbable polymer for the purpose of producing a surgically implantable device that will disintegrate in the body at a faster rate. An illustration of such knowledge is found in European Patent Application No. 0050215, published on Apr. 23, 1982.

It is known to reinforce one type of absorbable polymer with discrete elements such as fibers of another type of absorbable polymer having a higher melting point than the matrix polymer. For instance, see U.S. Pat. No. 4,279,249, to Vert et al.

DETAILED DESCRIPTION OF THE INVENTION

The sodium chloride or potassium chloride filler is used in the invention in finely divided form. For instance, the particle size of the salt is usually from about 10 to about 100 microns. The salt is used in an amount that is effective to enhance at least one property of the polymer, either a mechanical property, a physical property such as absorption rate, or simply to enhance the processing characteristics of the polymer. For instance, the salt will usually be used in amounts within the range of from 10 to about 60 percent, based on weight of polymer. The actual proportion of salt may vary widely from one case to the next, depending on the nature of the polymer, the particle size of the salt, the property which is desired to be enhanced and the degree of enhancement desired, and other similar considerations. In any event, the actual amount has not been found to be narrowly critical.

The salt can be employed with a wide variety of absorbable polymers. For instance, it can be employed with glycolide polymers and glycolide/lactide copolymers, dioxanone homopolymers and copolymers such as poly-1,4-dioxanone, and many other absorbable polymers. The absorbable polymers that can be used in the invention are described, for instance, in U.S. Pat. Nos. 4,052,988, 3,839,297, and 3,297,033, the disclosures of which are incorporated herein by reference.

The salt is added to the polymer at any convenient point in the processing of the polymer. For instance, in one mode of operating, a mixture of salt powder and powdered polymer in the desired proportions is first mixed to obtain a uniform mixture, and is then subjected to processing to form the desired surgical article. Such processing can be extrusion, compression molding, and the like.

The following examples illustrate the invention:

EXAMPLE 1

Sodium chloride (conventional table salt) was ground to a finer particle size by a mortar and pestle, and was then mixed with poly-1,4-dioxanone by the following procedure:

The polymer was melted in a reactor, and then the salt was added in an amount of 20 weight percent (based on weight of polymer). The salt powder was added slowly, followed by mixing so that good dispersion of the salt was achieved. The melted samples were cooled, frozen with liquid nitrogen, and then ground. The samples were then injection molded into "dog-bone" tensile specimens. The specimens were then subjected to a variety of physical testing procedures as molded, after annealing for 24 hours at 85° C., and after immersion (In Vitro) for 24 hours at 37° C. in buffered aqueous salt solution. The results of the physical tests are shown below in Table I. The sample labelled "control" was the poly-1,4-dioxanone polymer containing no reinforcing agent.

TABLE I

|  | Yield Strength | | | Yield Elongation | | Modulus | |
| --- | --- | --- | --- | --- | --- | --- | --- |
|  | $F_{kg}$ | $F_{lb}$ | PSI | Time | % | #kg | PSI |
| As Molded | | | | | | | |
| Example 1 | 24 | 52.9 | 3630 | 26.8 | 35.6 | 69.6 | 39,440 |
| Control | 26.5 | 58.5 | 4010 | 15.4 | 20.6 | 42 | 23,790 |
| Annealed | | | | | | | |
| Example 1 | 30.4 | 66.8 | 4570 | 12.5 | 15.4 | 75.8 | 43,000 |
| Control | 35.4 | 77.4 | 5290 | 15.0 | 19.6 | 62.6 | 35,390 |
| In Vitro | | | | | | | |
| Example 1 | 16.7 | 58.7 | 3960 | 15 | 19.6 | 38.4 | 21,410 |
| Control | 33.3 | 73.3 | 5000 | 16 | 21.3 | 45 | 25,350 |

The increase in modulus, both "As Molded" and after annealing, of the salt-filled samples compared with the unfilled Control, illustrates the increase in stiffness that is obtained by practicing the invention.

Another feature of the invention is that the absorption rate of the salt-filled polymer can be more precisely controlled, compared with the unfilled polymer. This is because the salt dissolution rate is more predictable than is the hydrolysis rate of the absorbable polymer. As a general rule, the absorption rate will be more rapid with the salt-filled polymers than with the unfilled polymers. This is caused by the greater surface area of polymer that is exposed to bodily fluids as the salt is leached out. A more rapid rate of absorption is a distinct advantage in some cases where strength is needed for only a relatively short time (i.e., days rather than weeks). Illustrations include some ligating clips, staples, anastomotic devices, and the like.

One valuable attribute of the invention is that, in at least some cases, the salt enhances certain processing characteristics of the polymer. With respect to poly-1,4-dioxanone, for instance, because of its crystalline nature (and concommitant rather sharp melting point), this polymer (unfilled) should be injection molded at a temperature within the narrow range of from about 118° to 125° C. in order to obtain optimum properties. Below 118°, its viscosity is quite high so that it fills the mold only with difficulty. Above 125°, its viscosity is so low that the polymer tends to flow out of the seams in the mold.

However, when, for instance, 40 weight percent sodium chloride is added as a filler, the injection molding temperature range for optimum properties is enlarged to a range of about 110° to 140° C. This is obviously a valuable attribute. Also shrinkage of the compression molded parts is reduced or eliminated by using the salt filler, and flash formation at the seams of the molds is also reduced or eliminated. These are also valuable attributes.

What is claimed is:

1. A composition comprising a synthetic absorbable polymer capable of being absorbed by the body containing as a filler finely divided sodium chloride or potassium chloride in an amount sufficient to enhance at least one property of the polymer.

2. The composition of claim 1 wherein the synthetic absorbable polymer is a lactide polymer, a lactide/glycolide polymer, or a dioxanone polymer.

3. The composition of claim 2 wherein the polymer is poly-1,4-dioxanone.

4. The composition of claim 1 in the form of an anastomotic device, a staple, or a ligating clip.

5. The composition of claim 1 wherein the filler is finely divided sodium chloride.

6. In a process for injection molding poly-1,4-dioxanone, the improvement which comprises employing poly-1,4-dioxanone containing finely divided sodium chloride or potasium chloride filler in an amount sufficient to significantly increase the temperature range within which injection molding of poly-1,4-dioxanone can be carried out.

* * * * *